US006136271A

United States Patent [19]
Lorincz et al.

[11] Patent Number: 6,136,271
[45] Date of Patent: Oct. 24, 2000

[54] SOLID STATE APPARATUS EMPLOYING HALL EFFECT SENSORS FOR DETECTING THE COAGULATION OF BLOOD

[75] Inventors: Robert S. Lorincz, Milltown; Richard Hall, Bernardsville, both of N.J.

[73] Assignee: International Technidyne Corporation, Edison, N.J.

[21] Appl. No.: 09/027,934

[22] Filed: Feb. 23, 1998

[51] Int. Cl.[7] .................................................. G01N 33/49
[52] U.S. Cl. .............................. 422/73; 436/69; 73/64.41
[58] Field of Search ...................... 422/73, 69; 436/149, 436/150, 151; 73/64.41, 54.01, 54.23, 54.28

[56] References Cited

U.S. PATENT DOCUMENTS

| | | |
|---|---|---|
| 3,492,096 | 1/1970 | Hattersley . |
| 3,520,659 | 7/1970 | Steinberg et al. . |
| 3,695,842 | 10/1972 | Mintz . |
| 3,836,333 | 9/1974 | Mintz . |
| 5,154,082 | 10/1992 | Mintz . |
| 5,289,255 | 2/1994 | Mullin et al. . |

*Primary Examiner*—Timothy M. Speer
*Assistant Examiner*—Jennifer McNeil
*Attorney, Agent, or Firm*—Arthur L. Plevy; Buchanan Ingersoll PC

[57] ABSTRACT

There is disclosed a system for detecting and timing the coagulation of blood from a liquid to a clot. The system comprises a vessel containing blood, a member of ferromagnetic material disposed within the vessel, means for providing relative motion between the vessel and the member, and a plurality of Hall effect sensors coupled through the walls of the vessel for sensing the strength of the magnetic flux lines and varying the electrical conductance upon change in the magnetic flux lines when the blood transforms itself and the member changes position relative to the plurality of sensors.

20 Claims, 9 Drawing Sheets

SOLID STATE APPARATUS EMPLOYING HALL EFFECT SENSORS FOR DETECTING THE COAGULATION OF BLOOD

FIELD OF THE INVENTION

The present invention relates in general to an apparatus and system for detecting the coagulation of blood, and in particular to microprocessor-controlled apparatus for detecting changes in a magnetic field adjacent to a zone containing a blood or plasma sample, which changes indicate that the blood has coagulated.

BACKGROUND OF THE INVENTION

The formation of clots within the circulatory system has been known to result in serious, if not fatal, consequences, particularly when the clot lodges within the heart or the brain. To prevent clots from occurring, coagulation inhibiting agents are normally administered to a patient. As a prerequisite for administering the coagulation inhibiting agents, the level of inhibiting agents within the patient's circulatory system must be known. The time required for clot formation within a standard laboratory test tube has been interpreted as an indication of the level of such inhibiting agents within a patient's circulatory system.

A system and a method for automatically measuring clotting time is disclosed in U.S. Pat. No. 3,695,842 entitled "METHOD AND SYSTEM FOR ANALYZING A LIQUID", issued to Michael D. Mintz on Oct. 30, 1972 and assigned to International Technidyne Corporation, the assignee of the present invention. A sample of blood is placed in a test tube and a permanent magnet is immersed in the blood sample. A magnetic reed switch, which is normally open, is positioned directly below the magnet. Flux lines, provided by the magnet, pass through the reed switch, causing it to close. Then, a relatively rotational motion is produced between the test tube and the magnet to agitate the blood, during which time the magnet remains positioned over the reed switch. When the blood coagulates, the resulting fibrous strands of clotted sample causes the magnet to move conjointly with the test tube. Thus, the magnet is displaced from the reed switch. This displacement causes a reduction in the density of the magnetic flux lines passing through the reed switch (i.e. weakens the magnetic field). As a result, the reed switch opens and a signal is generated, indicating the occurrence of the coagulation of blood.

An improved system for measuring clotting time is disclosed in U.S. Pat. No. 3,836,333 entitled "SYSTEM FOR TIMING THE COAGULATION OF BLOOD" issued to Michael D. Mintz on Oct. 30, 1972 and assigned to International Technidyne Corporation. An electromagnetic bias coil, which is wound around the reed switch, provides steady-state magnetic flux lines that supplement the flux lines provided by the permanent magnet. When the density of the flux lines passing through the reed switch decreases as a result of the magnet being displaced, the reed switch opens. The bias coil also provides a magnetic pulse, which forces the reed switch to a closed state. This system is manufactured under the trademark HEMOCHRON by International Technidyne Corporation at Edison, N.J.

The precision with which the system detects the coagulation of blood is dependant upon the ability of the reed switch to respond to changes in density of the magnetic flux lines. To ensure that the reed switch opens and closes in the presence of the correct flux densities, the reed switch must be manufactured with a great deal of precision. When tested, any reed switch that does not operate as specified must be eliminated. This results in additional expense as high precision switches are inherently more costly.

One problem encountered in using a reed switch for magnetic field measurement relates to the process of magnetic hysteresis. The effect of hysteresis in a reed switch is to require a greater magnetic flux density to initially close the reeds than that required to simply maintain the reeds in a closed condition. In the system described above, the difference between the magnetic field required to close the reeds and the magnetic field at which the reeds just reopened must be less than the difference in magnetic field passing through the reed switch when the magnet has been displaced relative to the reed switch.

A second problem with reed switches relates to magnetic storage or magnetization. The reeds of the switch are made of a ferromagnetic material. During operation, when magnetic flux lines pass through the reed switch, the reeds store energy at a slow rate and therefore, become magnetized. As a result of the stored magnetic energy, the reed switch becomes a time-dependent storage device, which may fail to open or close precisely at predetermined external flux level. Thus, a reed switch employed in the system described above may not switch states precisely when the blood clots.

Still a further improvement for detecting the coagulation of blood is disclosed in U.S. Pat. No. 5,154,082 entitled "MICROPROCESSOR-CONTROLLED APPARATUS AND METHOD FOR DETECTING THE COAGULATION OF BLOOD" issued to Michael D. Mintz on Oct. 13, 1992 and assigned to International Technidyne Corporation. In this patent a microprocessor calibrates the reed switch by adjusting the density of the magnetic flux lines from an adjustable source so that the reed switch is open when the ferromagnetic member reaches a predetermined distance of displacement. However, problems also exist with this improved device as well, since the biased reed switch acting as a clot detector timer is unable to determine the exact position of the magnet at a given point in time. The reed relay design only detects the presence of the calibrated field strength within the test well and not its position. Knowledge of the exact position of the magnet within the test tube would permit the actual clot time to be empirically extrapolated, as well as actually detected. A still further problem associated with the prior art analog base designs is the need to precisely calibrate using an empty test well each of the systems in order to accurately measure and detect the blood clotting. Moreover, because of the analog nature of the prior design of the prior art, the use of the reed relay and field coil bias apparatus causes signal drift and may result in miscalibration of the analog test well. Still further, the prior art uses, in addition to reed relay switches and wire coils, thermistors as the heating mechanism and temperature sensors. Each of these analog components are both difficult to manufacture and costly. Accordingly, a test well which can accurately track magnetic position, rate of magnet movement, ratio of movement from and to multiple positions, as well as provide detailed viscometry changes and accurate clotting information while eliminating signal and field strength drift, in addition to easing construction and lowering the cost, is highly desirable.

SUMMARY OF THE INVENTION

The disadvantages of the prior art systems for detecting the transformation of blood from a liquid to clot are overcome by the present invention. The present invention describes a system for detecting and timing the coagulation of blood from a liquid to a clot comprising a vessel containing blood; a member of ferromagnetic material disposed within the vessel; means for providing relative motion between the vessel and the member; and a plurality of Hall effect sensors coupled through the walls of the vessel for sensing the strength of the magnetic flux lines and varying the electrical conductance upon change in the magnetic flux lines when the blood transforms itself and the member changes position relative to the plurality of sensors.

DETAILED DESCRIPTION OF THE INVENTION

Figure 1:
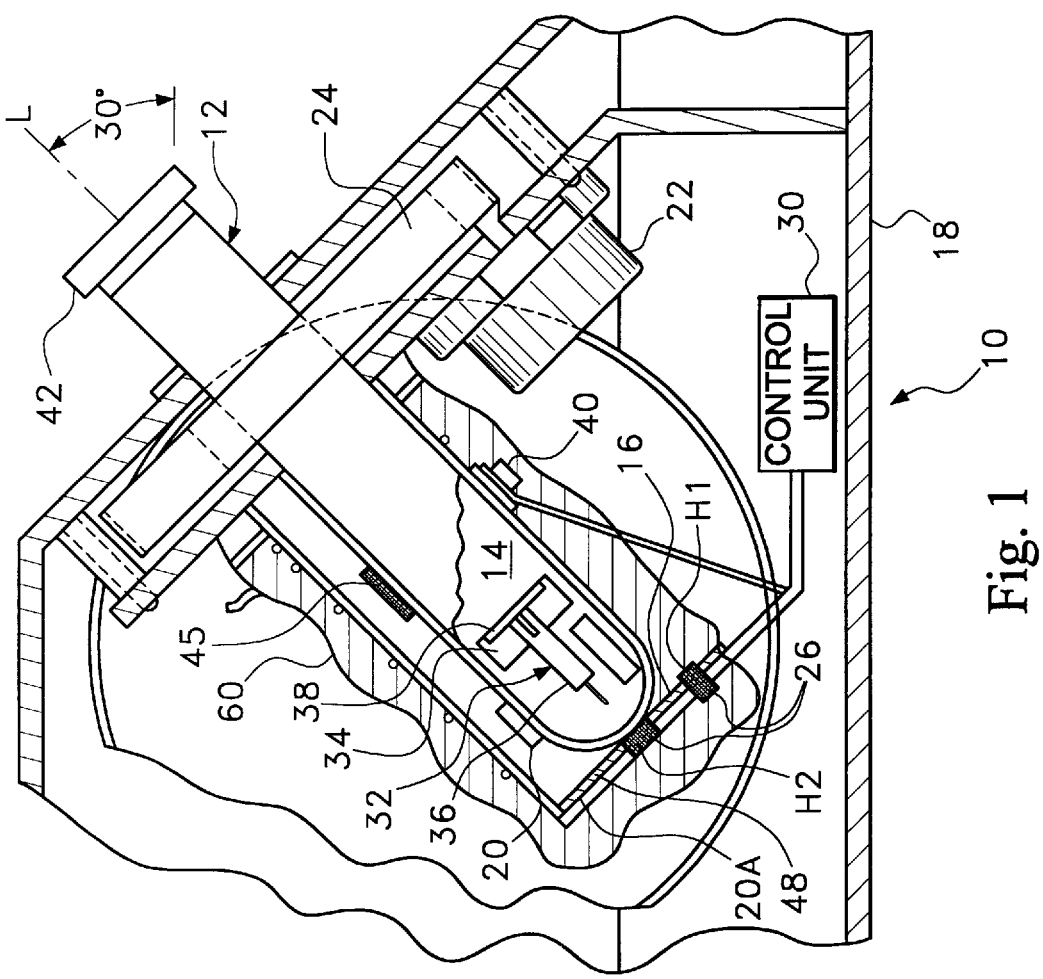
FIG. 1 is a cross-sectional view of a system for detecting the coagulation of blood in accordance with the present invention.

Referring to FIG. 1, there is shown a system 10 for detecting the coagulation of blood according to the present invention. Throughout the drawings of FIGS. 1, 7, 8, and 9, like reference numerals are used to indicate like elements. The system 10 comprises a test tube 12, which contains a sample of blood 14 to be tested, a bar magnet 16 which is the preferred embodiment, is cylindrical or spherical, and which is immersed in the blood 14, and an analyzer 18, which includes test well 20 for receiving the test tube. A layer of insulation 60 surrounds the test tube and test well 20 to secure the device and is maintained within shell test well 70 (FIG. 8) encapsulates the tube. The test tube 12 is inserted into the test well 20 having a closed bottom surface 20A, thereby encapsulating a portion of the tube, where its longitudinal L is inclined at approximately 30° from horizontal. Gravity causes the magnet 16 to settle to the lowest position of the test tube 12, hereinafter referred to as the initial position. The analyzer 18 includes a drive motor 22, which is provided with a transmission 24 for rotating the test tube 12 about its longitudinal axis L. Hall effect sensors 26 which form part of the analyzer 18 are located preferably beneath test tube 12 (and therefore beneath magnet 16) and positioned on a top surface of plate 48 located on the outside surface of test well 20 for sensing the relative magnetic flux from magnet 16. The design and operation of Hall effect sensors is well-known, and will not be described here, except in conjunction with the overall operation of the system 10. Plate 48 on which Hall sensors 26 are disposed is preferably made of plastic and provides mechanical support for the sensors.

Figure 2:
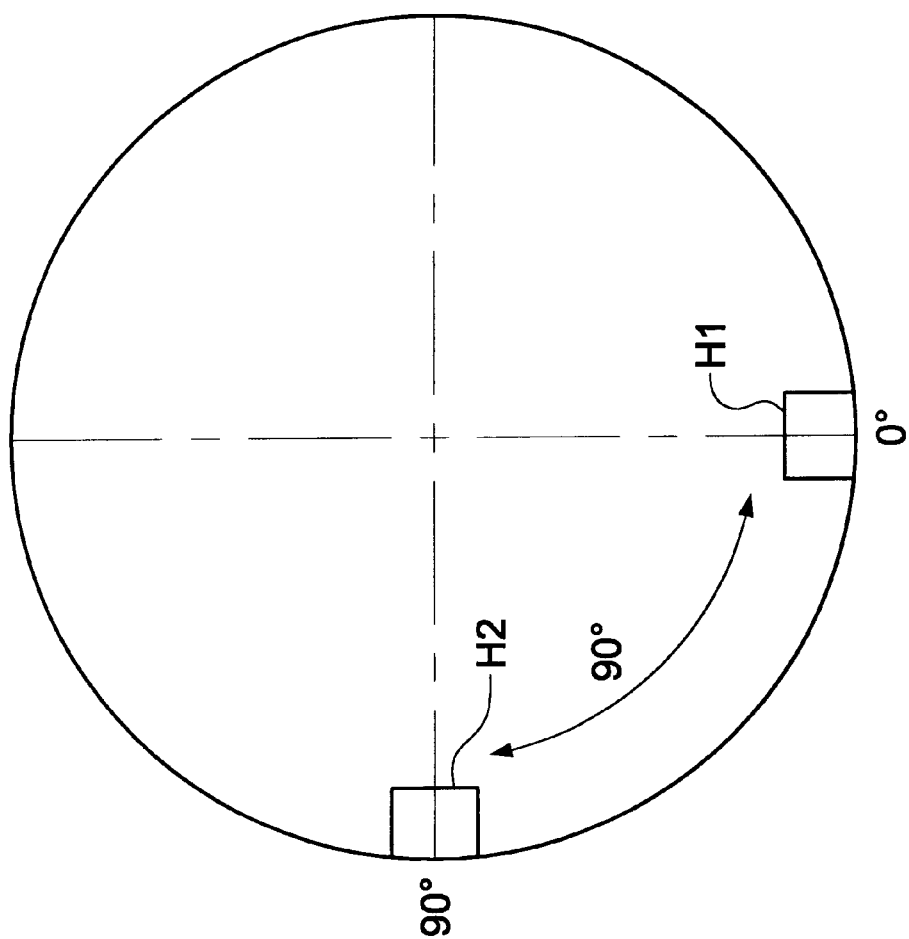
FIG. 2 is a plate end view of the positions of Hall effect sensors shown in FIG. 1 in accordance with an embodiment of the present invention.

FIG. 2 shows a plate end view of the Hall sensors H1 and H2 disposed on plate 48 and attached to cylindrical test well 20. As shown in a preferred embodiment in FIG. 2, Hall sensors H1 and H2 are fixedly positioned at 90° with respect to one another to provide a precise calibration reference position from which to measure the relative magnetic field strengths received at each of these locations from magnet 16. The flux lines provided by the magnet 16 from its position within the test tube at any given instant are received by each of the Hall sensors and converted into an analog signal indicative of the strength of the magnetic field relative to each of the fixed positions of the sensors H1 and H2. Each of the analog signals output from Hall sensors H1 and H2 are received by control unit 30 which converts the analog signals to digital format via A/D conversion to provide a digital voltage corresponding to the relative magnetic field strength (and hence relative position of magnet 16) received at each of the sensors H1 and H2. In this manner, the control unit is operative to determine the exact position of the magnet 16 at any point within the magnetic field (clot) detection area. Since the present invention employs the Hall effect sensors which are solid state devices, having no moving parts, such devices do not drift; unlike the reed relay and field coil bias devices utilized in the prior art. Further, by knowing the exact position of the magnet within the test tube, actual clot time may be empirically extrapolated, as well as actually detected. This provides more accurate tracking method and magnetic rate movement, as well as more detailed viscometry changes to provide accurate clotting information.

As previously mentioned, the analytic operation of the system 10 is controlled automatically by a control unit 30. The control unit 30 commands the drive motor 22 to rotate the test tube 12 about its longitudinal axis L. In the unclotted condition, blood 14 behaves as a liquid (i.e., the unclotted blood 14 does not support shear forces) and therefore, the magnet 16 does not rotate with the test tube 12. As a result, there is produced a relative motion between the test tube 12 and the magnet 16.

Immediately after commanding the drive motor 22 to rotate the test tube 12, the control unit 30 energizes the sensors H1 and H2. The magnetic flux densities produced by magnet 16, and unshielded ambient conditions (i.e. magnetic fields produced by the drive motor 22, other electromagnetic equipment and the earth's field) are added vectorial to produce the total effective magnetic flux density acting on the sensors H1 and H2. For simplicity, however, only the flux densities of the magnet 16 shall be considered. The magnetic flux density from magnet 16 is sensed by Hall sensors H1 and H2 at each of their fixed positions and analog signals indicative of the field strength are transmitted to unit 30.

In the preferred embodiment, the test tube is rotated at 1 RPM. Knowledge of the rotation speed, coupled with temporal feedback of the detected magnetic field strengths from each Hall sensor enables the determination of magnet position within the test tube, as well as extrapolating clotting times based on an analysis of prior Hall sensor data over a predetermined time interval. The control unit 30 which includes a microprocessor and a A/D converter, samples each of the analog signals output from the Hall sensors, and performs level quantization upon each of the samples to provide a digital voltage output representation of the relative field strength and hence, position of the magnet.

Figure 3:
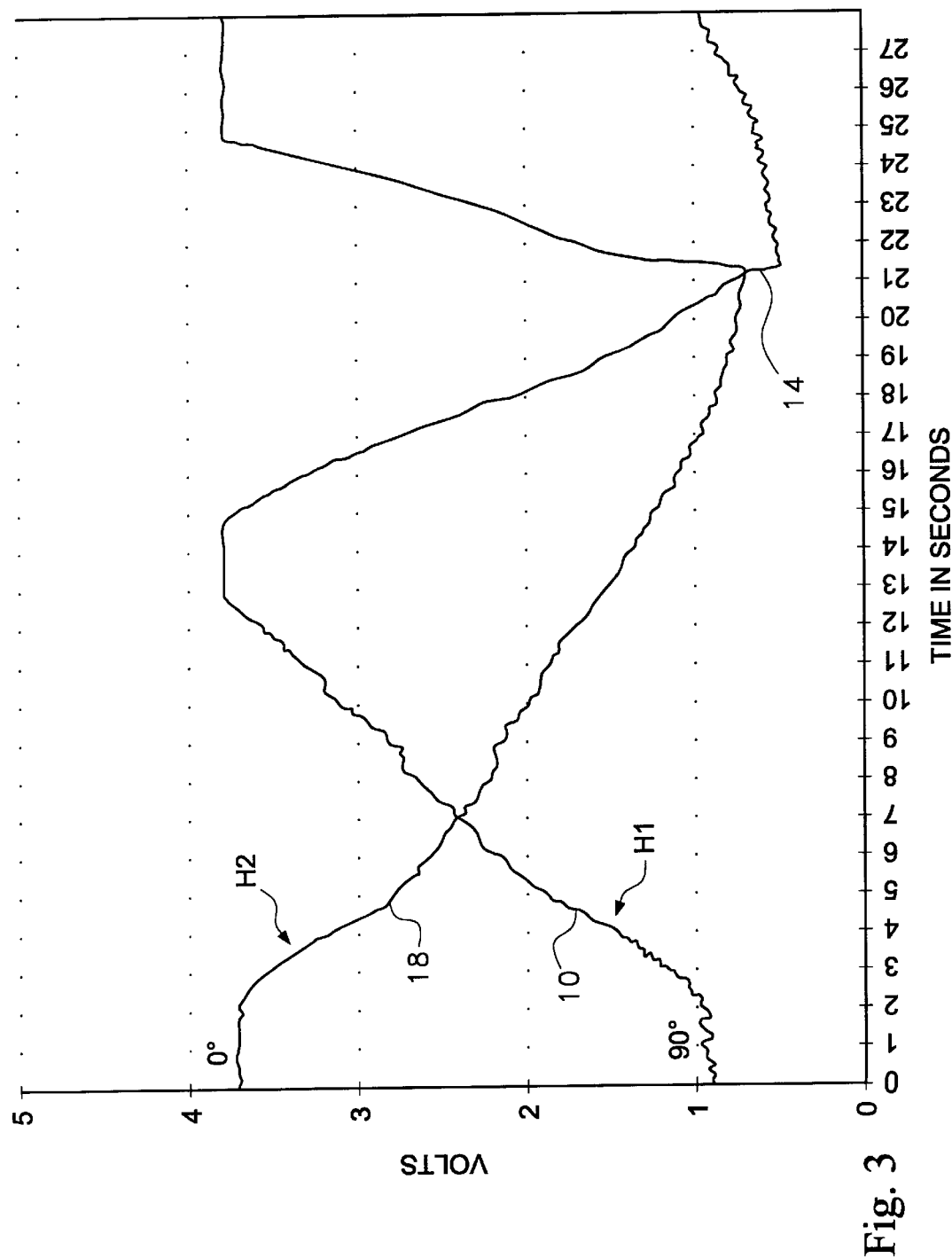
FIG. 3 is a plot of the electrical signals from Hall sensors H1 and H2 of the relative strength of the electrical signals from H1 and H2 as a function of time.

FIG. 3 shows a plot of the electrical signals from the H1 and H2 sensors as a function of time for a sample of blood immersed in a test tube of 100% diluent PT and plasma. T he basic concept is that given the known relative offset of the sensors (i.e., 90° with respect to each other) the magnet position may be tracked by sampling each of the sensor values and comparing the magnetic field relative strength at each time instant to determine magnet movement, and hence, clotting time.

From FIG. 3, one can ascertain that when the magnet is at 0°, H1 reads ≈0.95 Vdc at 0 seconds and climbs to ≈3.75 Vdc at 22.5 seconds. The 90° H2 sensor shows the same effect. The steepness of the two slopes of the H1 and H2 curves (ref. numerals 10, 18) indicate a blood clot at 13 to 14 seconds. This sensor system allows the instrument to exactly track the magnet position within the test well. At 21 seconds (ref. numeral 14) the plot shows that magnet 16 has reached the top of its travel and fallen back to the 0° position for H1. The Hall effect sensing system 10 (FIG. 2) is far superior to the original magnet reed-relay method because it can dynamically locate the magnet at any point within the test well while the reed-relay can only detect a clot endpoint. With the Hall effect method blood clots can be determined and extrapolated prior to the actual clotting time. This could also be used to detect platelets. Since the clotting time can be predicted faster, the actual surgical time may be shortened, minimizing patient trauma, infection and recovery.

Figure 4:
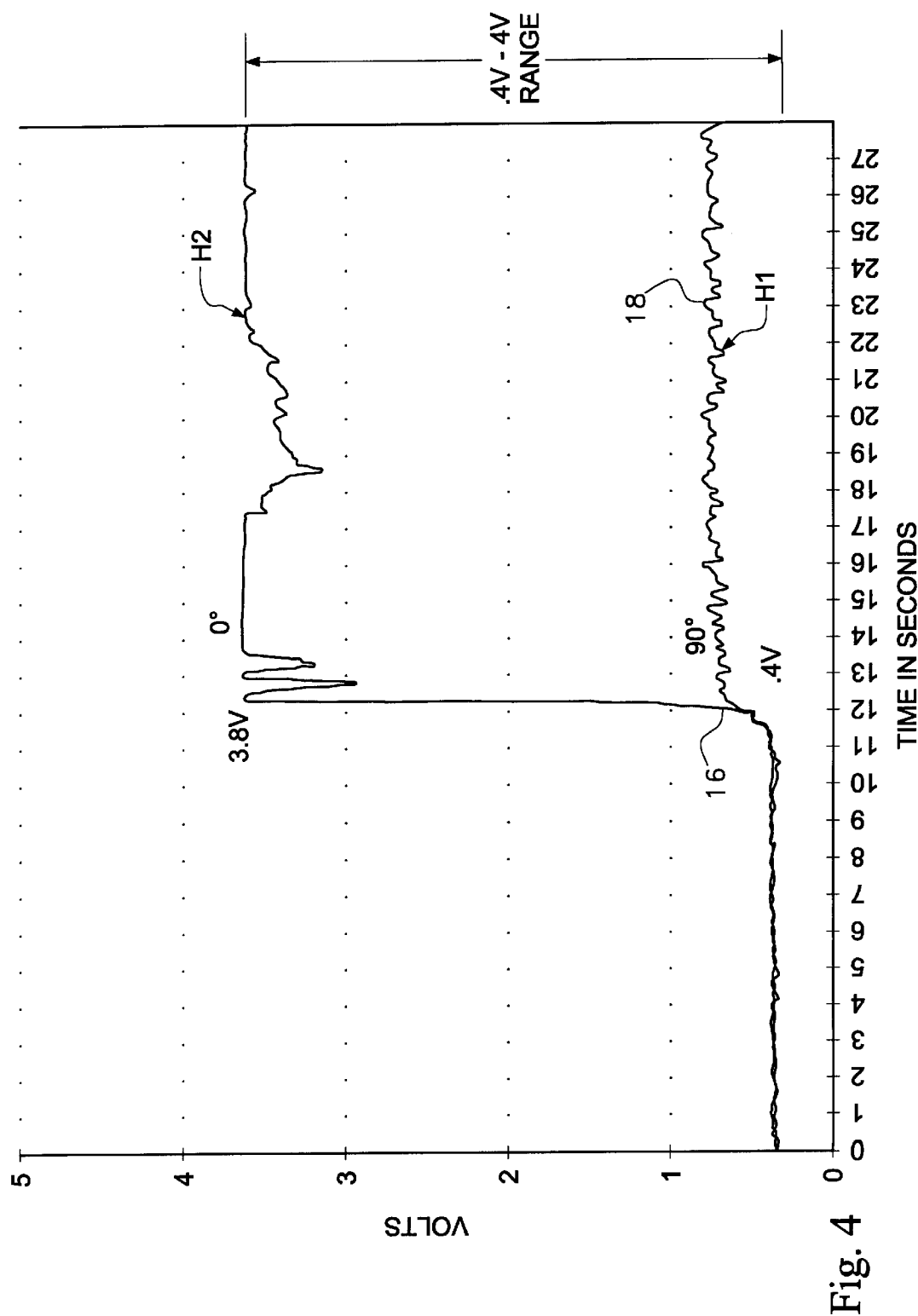
FIG. 4 is a plot of the electrical signals from H1 and H2 Hall sensors when a magnet is inserted into an empty test well.
Figure 5:
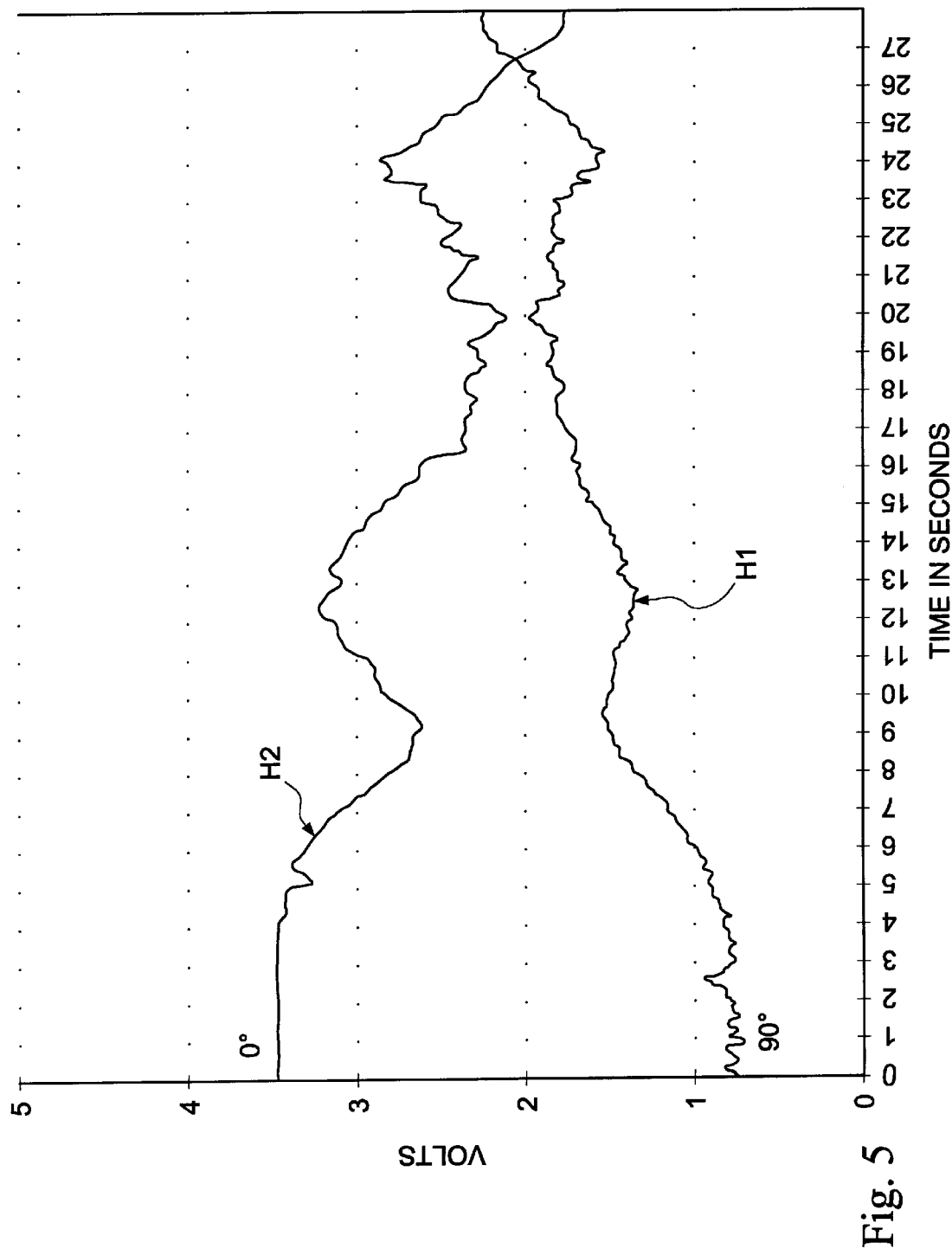
FIGS. 5 and 6 are illustrative plots of the Hall sensors H1 and H2 to determine clotting time for various dilute ratios.
Figure 6:
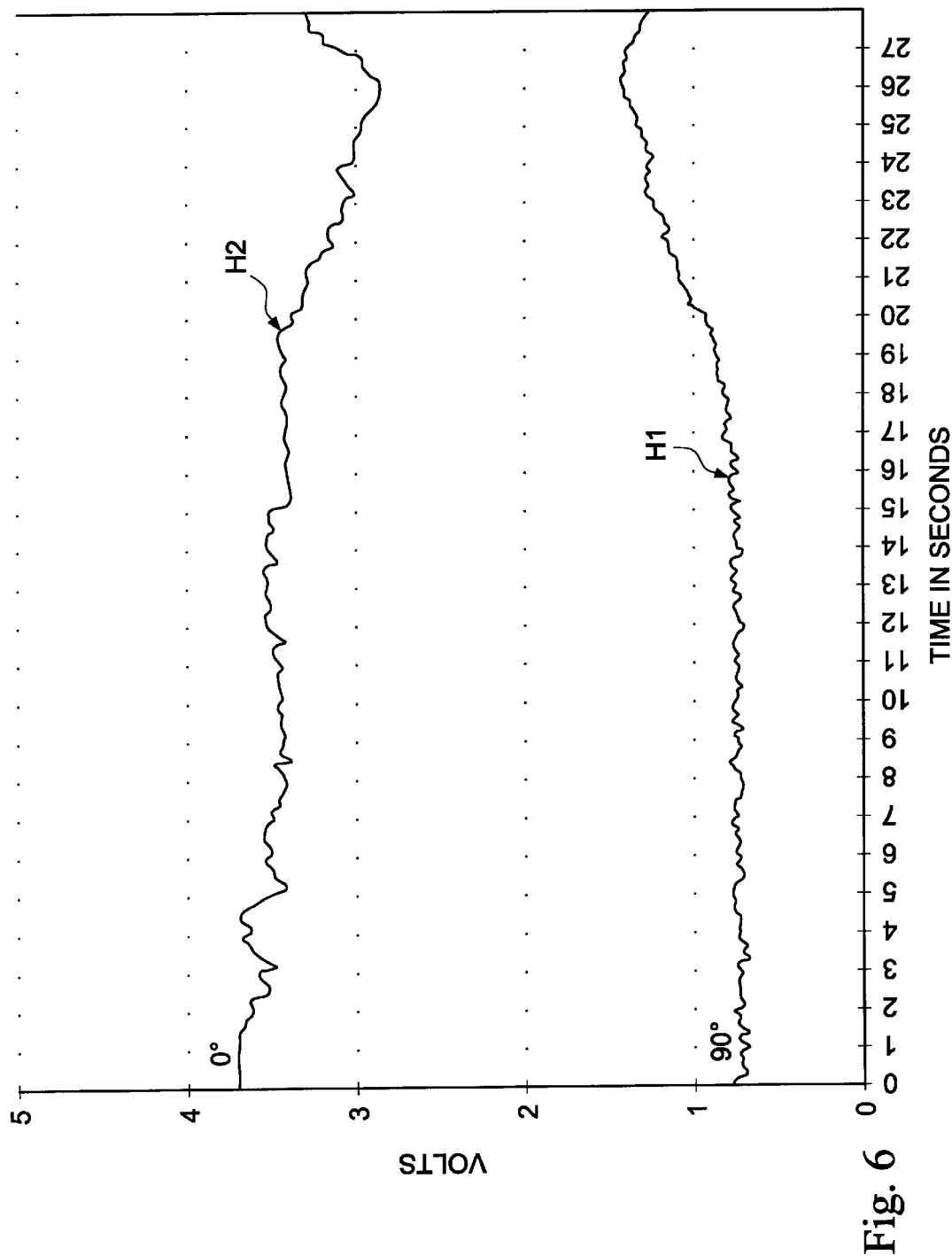

Referring now to FIG. 4, there is shown the H1 and H2 signals when the magnet is inserted into an empty test well at 13 seconds (ref. numeral 16). Prior to that time, only ambient signals were sensed by H1 and H2. Note that under no magnetic stimulus, each channel produces 3.75 volts. As the flux of the magnetic field increases, the voltage drops. Ref. numerals 16 and 18 corresponding to a time period of 16 seconds, shows the voltage range between the minimum and maximum signal strengths H1 and H2 is 0.4Vdc to 3.8Vdc. Figures indicative of clot detection and tracking shown in FIG. 2 are similarly illustrated in FIGS. 5 and 6. FIG. 5 shows a clotting profile with a 20% PT & Plasma Diluent. FIG. 6 shows a clotting profile with a 10% PT & Plasma diluent. The more dilute the ratio, the more subtle the clot. As one can see from the above diagrams, the Hall effect system has to ability to detect the "weak" clots while the reed-relay method will only detect a clotting endpoint.

The operation of the solid state test well device of the present invention is now described with reference again made to FIG. 1. The magnet 16 remains substantially in its initial position within the test tube 12 until the formation of a fibrous strand of clotted sample. Note that use of an agent to interact with the blood sample and assist in the clotting process and having a particular plasma diluent ratio is a preferred approach in deterring the clot time. The clotted sample functions to adhere the magnet 16 to the rotating wall of the test tube 12. When the adhesive forces of the clot are sufficient to overcome the gravitational and magnetic forces, the test tube 12 pulls the magnet 16 away from its initial position and causes a change in the density of the magnetic flux lines received by each of the sensors.

This causes one of the sensors (i.e., H1) to sense a smaller magnetic field and hence, voltage increases. Therefore, an increased electrical signal from H1 results because the magnet is farther away from H1 due to its change in position. While the second Hall sensor H2 may sense an increase in the magnetic flux density as a result of a more proximal distance to the magnet. In this manner, the tracking of the magnet within the test well may be accurately determined.

Still referring to FIG. 1, the test tube 12 is a cylindrical vessel having a closed end and an open end. The test tube 12 is made of a nonferromagnetic material such as glass or plastic. The open end of the test tube 12 may be sealed by stopper 42. A blood sample 14 is injected into the test tube 12 through the open end. If the test tube is stoppered, the material of which the stopper is composed must be a soft plastic or elastomeric.

A plastic wedge 32 is located and frictionally engages the inner walls at the closed end of the test tube 12. Four rectangular shaped fins 34 extend radially from a central hub 36 and frictionally engage the walls of test tube 12. The central hub 36 is attached to a spacer disk 38, which retains the magnet 16 within the lower zone of test tube 12. The wedge 32 functions to displace the magnet 16. As the test tube 12 is rotated and the blood 14 has yet to coagulate, the magnet 16 remains relatively motionless. Once the blood 14 coagulates, however, the clot provides a mechanical "grip" which adheres one end of the magnet 16 to the wedge 32. Thus, as the test tube 12 and magnet 16 begin to rotate conjointly, the magnet 16 is pulled out of alignment with the central hub 36 of the plastic wedge 32 and attains an oblique angle with respect to longitudinal axis L. As a result, the magnet 16 "toggles" wherein each end of the magnet 16 touches a different point on the test tube 12 wall, and the center of magnet 16 contacts a point in the central hub 36 of wedge 32. Then, the wedge 32 helps displace the magnet 16 upwards and away from the initial position.

Figure 7:
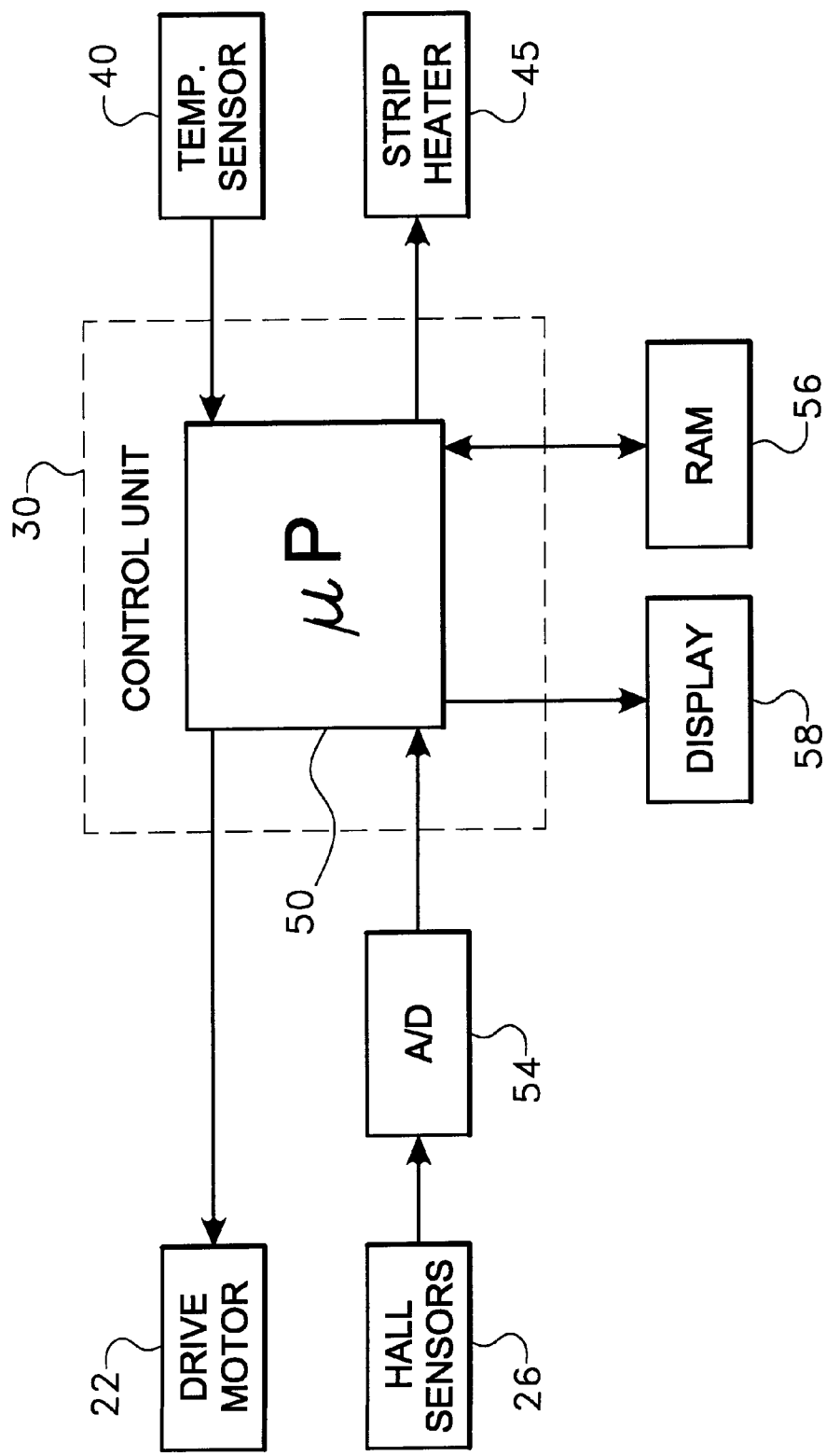
FIG. 7 is a schematic diagram of the control unit according to an embodiment of the present invention.

Referring now to FIG. 7, there is shown a schematic diagram of the control unit 30. The control unit 30 includes a microprocessor 50, which controls the operation of the drive motor 22, and monitors the signals from Hall sensors 26. The output of the sensors 26 are preconditioned and then connected to the microprocessor 50 through a analog-to-digital (A/D) converter 54. The microprocessor 50 further includes random access memory (RAM) 56 and a display unit 58, which displays the time measured for the blood sample 14 to clot. Since the general principles of construction of microprocessors are well known, selection of a particular type of microprocessor is left to those skilled in the art.

Referring again to FIGS. 1 and 7, a solid state temperature sensor 40 is coupled to an outer wall of test tube 12 for sensing the temperature of a blood within the test tube. The strip heater 45 is positioned along another portion of the outer wall of test tube 12, preferably opposite the temperature sensor 40, to heat the blood sample to the appropriate temperature, which in the preferred embodiment, such temperature is approximately 37° C. The adhesive heater strip 45 and solid state temperature sensor 40 function to replace the prior art heating mechanism of coil, wire and thermistor to provide a more accurate and lower cost heating and monitoring system. Both the temperature sensor and the strip heater are electrically coupled to the control unit microprocessor which receives the temperature from the sensor 40 and compares the temperature with the desired threshold setting. If the temperature sensed is less than the desired level, the microprocessor causes a control signal to be sent to the adhesive strip heater 45 to thermally activate the heater to increase the sample temperature. Upon reaching the desired temperature, the adhesive strip is deactivated. In the preferred embodiment, a PID controller is used to achieve a nominal temperature of 37° C.

Figure 8:
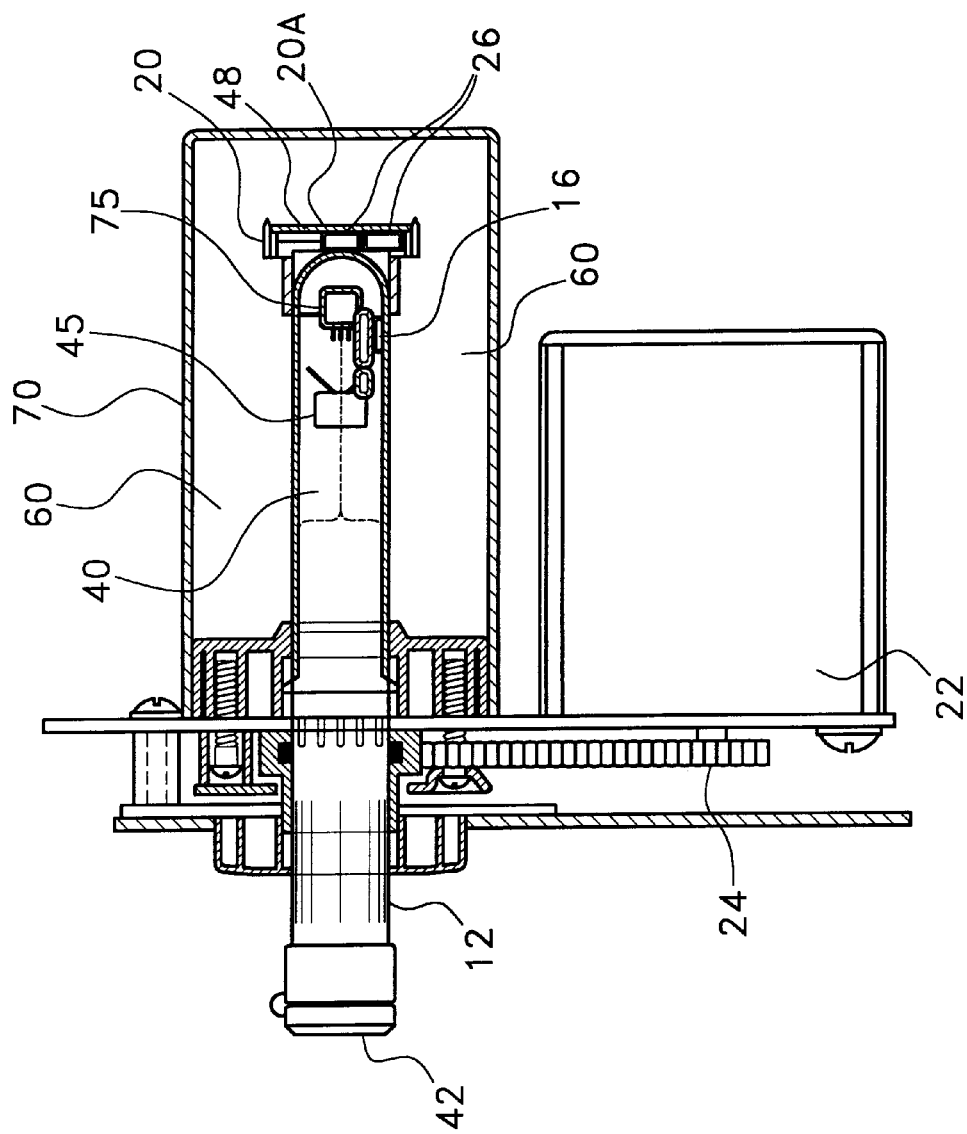
FIG. 8 is a schematic diagram of the blood coagulation system where the Hall sensors are mounted onto a plate within the test well.
Figure 9:
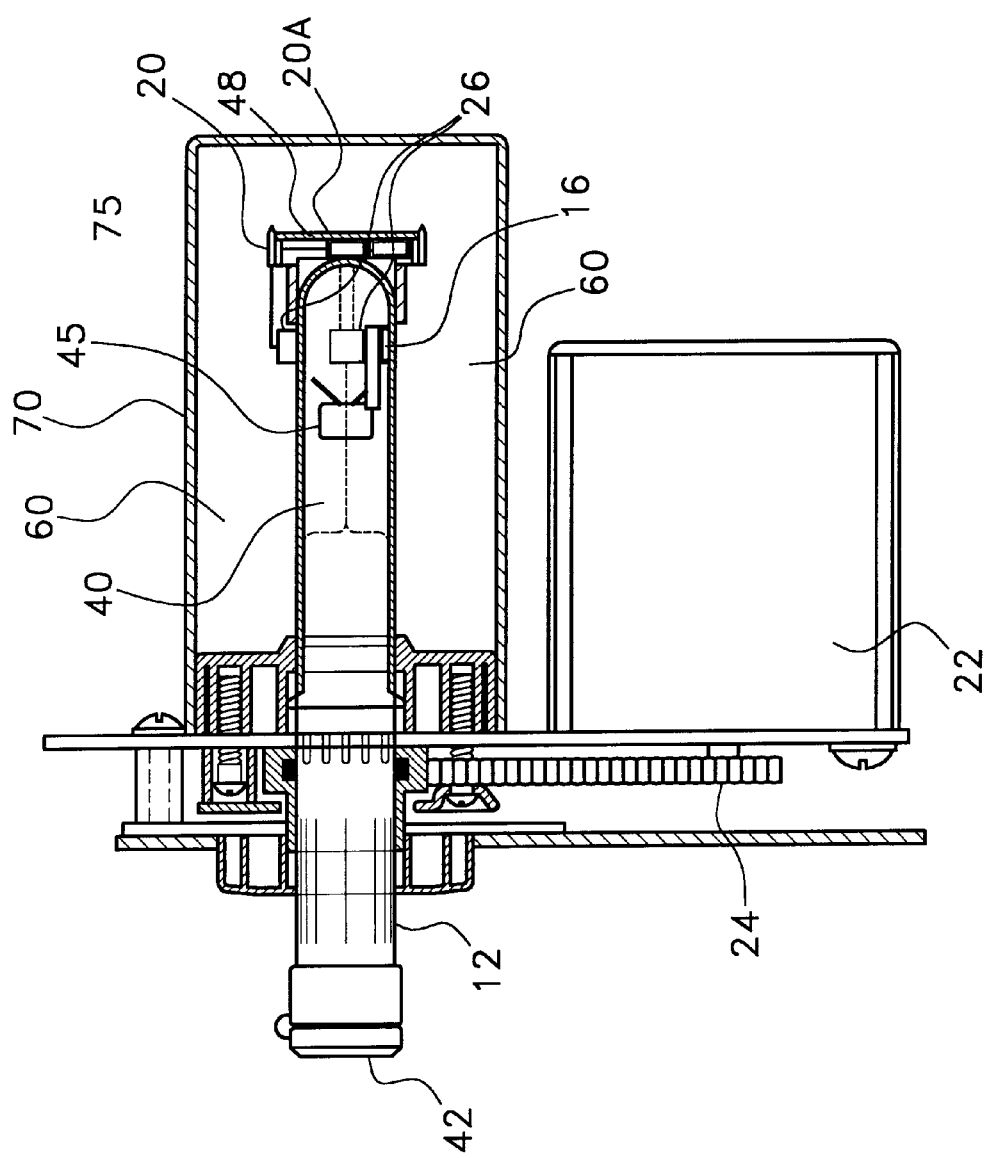
FIG. 9 is a schematic diagram of the blood coagulation system where the Hall sensors are mounted adjacent the test tube body.

As one can ascertain, the use of solid state Hall effect sensor devices within a magnetic test well permits electronics to determine the exact position of the magnet at any point within the clot detection area. Since the solid state devices have no moving parts and do not drift in contrast to the prior art reed-relay and field coil bias systems, little or no calibration of the system is necessary. Still further, knowledge of the exact position of the magnet within the test tube allows for the extrapolation of the actual clot time, as well as the determination of the actual clot time detected. Empirical extrapolation permits one to know well in advance of actual test completion whether or not the blood will coagulate within a particular time interval, thus saving significant time and minimizing the number of tests required to be rerun. It will be understood that the embodiment described herein is merely exemplary, and that a person skilled in the art may make many variations and modifications without departing from the spirit and scope of the invention. For example, while it has been shown that the Hall sensors are disposed on the outside of the test well 20, the sensors may also be disposed within the test well 20 with the metal or plastic plate also included within the well as shown in FIG. 8. Still referring to FIG. 8, this alternative embodiment shows the temperature sensor 40 comprising a thermistor located on the test tube for sensing the temperature of the blood sample and thermal fuse 75. Similarly, while the Hall sensors have been shown to be positioned underneath the test tube, they may also be positioned adjacent the tube body portion containing the blood sample for sensing magnetic flux changes, as shown schematically in FIG. 9. Furthermore, the plate may also be eliminated such that the sensors are disposed directly onto the well. Still further, while two sensors have been shown, each displaced 90° relative to one other, the sensors may be displaced at other orientations. In addition, constellations of Hall sensors having numbers greater than two, may also be positioned along the periphery of the well and various positions with each of the sensors measuring the magnetic fields, and transferring such electronic signal representations to the control unit of the microprocessor for determining magnetic positions, such as may be used in the detection of platelets, for example. All such modifications are intended to be included within the scope of the invention as defined in the appended claims.

What is claimed is:

1. A system for detecting and timing coagulation of whole blood or plasma from a liquid to a clot comprising:
   a vessel containing said blood or said plasma and having a longitudinal axis and at least one sidewall;
   a member of ferromagnetic material disposed within said vessel for producing magnetic flux;
   means for providing relative motion between said vessel and said member; and
   a plurality of Hall effect sensors being positioned in a plane substantially perpendicular with respect to said longitudinal axis and magnetically coupled to said member through the sidewall of said vessel for sensing a strength of said magnetic flux and providing a varying electrical output according to a change in said magnetic flux when the blood or plasma transforms itself and said member changes position relative to said plurality of sensors.

2. The system according to claim 1, wherein each said sensor produces an analog signal indicative of said magnetic field strength sensed, and wherein the combination of said signals is indicative of said position of said member in the vessel.

3. The system according to claim 2, further comprising control means coupled to said plurality of sensors having conversion means for converting said analog signals into digital signals indicative of said position of the member.

4. The system according to claim 3, said control means further including means for recording and displaying the changes for each sensor.

5. The system according to claim 4, said control means further including determination means for extrapolating the clotting time based on prior recorded changes in said flux.

6. The system according to claim 3, further comprising a solid state temperature sensor coupled to said side wall of said vessel and to said control means.

7. The system according to claim 6, further comprising an adhesive strip heater coupled to said side wall of said vessel and to said control means.

8. The system according to claim 3, wherein said control means includes a microprocessor.

9. The system according to claim 1, wherein said plurality of Hall sensors consists of 2 Hall sensors.

10. The system according to claim 9, wherein said Hall sensors arc displaced at 90 degrees from one another in said plane.

11. The system according to claim 1, wherein said Hall sensors are disposed on a second member disposed on a cylindrical test well which encapsulates said test tube.

12. The system according to claim 11, wherein the second member is plastic.

13. The system according to claim 11, wherein the second member is metal.

14. The system according to claim 11, wherein the second member is positioned on an interior surface of said test well.

15. The system according to claim 11, wherein the second member is positioned on an exterior surface of said test well.

16. A system for detecting and timing coagulation of blood or plasma from a liquid to a clot comprising:
   a vessel containing said blood or plasma and having at least one wall and a longitudinal axis;
   a magnet disposed within said vessel for producing magnetic flux;
   means for providing relative motion between said vessel and said magnet;
   a plurality of Hall effect sensors located at fixed positions in a plane being substantially perpendicular to said longitudinal axis of said vessel and being magnetically coupled to said magnet through the wall of said vessel for sensing the strength of said magnetic flux and providing time varying electrical signals indicative of a magnetic field strength upon change in said magnetic flux when the blood or plasma transforms itself and said magnet changes position relative to said plurality of sensors;
   a control unit responsive to said plurality of Hall effect sensors for receiving said time varying electrical signals, digitizing said signals, and providing a graphical display of the magnitude of each signal from each said Hall sensor as a function of time superimposed upon one another.

17. The system according to claim 16, further comprising a test well having a closed bottom surface containing said test tube.

18. The system according to claim 17, further comprising a plastic plate having a top surface on which each of said plurality of Hall sensors is mounted, and having a bottom surface mounted to said test well.

19. The system according to claim 18, wherein said plurality of Hall sensors comprises two Hall sensors positioned at an angle of substantially 90 degrees relative to one another.

20. The system according to claim 19, wherein said plastic plate is mounted to said test well such that said Hall sensors are located outside of said test well.

* * * * *